(12) United States Patent
Baltzer et al.

(10) Patent No.: US 7,582,664 B2
(45) Date of Patent: *Sep. 1, 2009

(54) ACYLAMINOTHIAZOLE DERIVATIVES, PREPARATION METHOD THEREOF AND USE OF SAME IN THERAPEUTICS

(75) Inventors: Sylvie Baltzer, Strasbourg (FR); Viviane Van Dorsselaer, Strasbourg (FR)

(73) Assignee: Sanofi-Aventis, Paris (FR)

( * ) Notice: Subject to any disclaimer, the term of this patent is extended or adjusted under 35 U.S.C. 154(b) by 313 days.

This patent is subject to a terminal disclaimer.

(21) Appl. No.: 11/456,123

(22) Filed: Jul. 7, 2006

(65) Prior Publication Data

US 2006/0293365 A1 Dec. 28, 2006

Related U.S. Application Data

(63) Continuation of application No. PCT/FR2005/00032, filed on Jan. 7, 2005.

(30) Foreign Application Priority Data

| Jan. 16, 2004 | (FR) | .................... 04 00387 |
| Jul. 22, 2004 | (FR) | .................... 04 08115 |

(51) Int. Cl.
*A01N 43/78* (2006.01)
*A61K 31/425* (2006.01)

(52) U.S. Cl. ...................... 514/365; 514/183; 514/359; 514/360; 514/370; 514/371

(58) Field of Classification Search .................. 514/371
See application file for complete search history.

(56) References Cited

U.S. PATENT DOCUMENTS

| 7,291,636 B2 * | 11/2007 | Baltzer et al. ............... 514/371 |
| 7,371,770 B2 * | 5/2008 | Baltzer et al. ............... 514/371 |
| 2004/0152747 A1 * | 8/2004 | Chen et al. .................. 514/370 |

FOREIGN PATENT DOCUMENTS

| WO | WO 98/22433 | 5/1998 |
| WO | WO 00/24392 | 5/2000 |
| WO | WO 03/014095 | 2/2003 |
| WO | WO 2004/009565 | 1/2004 |
| WO | WO 2004/033439 | 4/2004 |

OTHER PUBLICATIONS

Chemical Encyclopaedic Dictionary, Moscow, Sovetskaya Encyclopedia, (1983), pp. 130-131.

* cited by examiner

*Primary Examiner*—Patrick T Lewis
(74) *Attorney, Agent, or Firm*—Balaram Gupta

(57) ABSTRACT

The invention relates to a compound of formula (I):

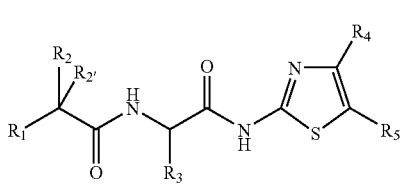

Wherein $R_1$, $R_2$, $R_{2'}$, $R_3$, $R_4$ and $R_5$ are as defined herein. The invention also relates to the use of said compound in therapeutics.

20 Claims, No Drawings

ACYLAMINOTHIAZOLE DERIVATIVES, PREPARATION METHOD THEREOF AND USE OF SAME IN THERAPEUTICS

CROSS REFERENCE TO RELATED APPLICATIONS

This application is a continuation of International application No. PCT/FR2005/000,032, Jan. 7, 2005, which is incorporated herein by reference in its entirety; which claims the benefit of priority of French Patent Application No. 04/00,387, filed Jan. 16, 2004 and French Patent Application No. 04/08,115, filed Jul. 22, 2004.

BACKGROUND OF THE INVENTION

1. Field of the Invention

The present invention relates to acylaminothiazole derivatives and to their preparation and their therapeutic use.

2. Description of the Art

Compounds derived from acylaminothiazole, described in documents WO 03/014095 A, WO 2004/009565 A and WO 2004/033439 A, which are inhibitors of formation of the β-amyloid (β-A4) peptide, are already known. All of the references referred to hereinabove are incorporated herein by reference in their entirety.

There is still a need to find and develop products that are inhibitors of the formation of the β-amyloid (β-A4) peptide. The compounds of the invention satisfy this aim.

SUMMARY OF THE INVENTION

A first subject of the present invention is a compound corresponding to the general formula (I):

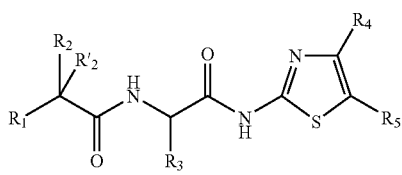

in which $R_1$ represents:

either a $C_{1-6}$ alkyl optionally substituted with one to three substituents chosen from a halogen, a trifluoromethyl, a hydroxyl, a $C_{1-6}$ alkoxy, a $C_{1-6}$ thioalkyl, a thiophene or a phenyl; or a $C_{3-7}$ cycloalkyl, a thiophene, a benzothiophene, a pyridyl, a furyl or a phenyl; the said phenyl groups being optionally substituted with one to three substituents chosen from a halogen atom, a $C_{1-6}$ alkyl, a $C_{1-6}$ alkoxy, a hydroxyl, a methylenedioxy, a phenoxy, a benzyloxy or a trifluoromethyl;

$R_2$ and $R'_2$ represent, independently of each other, a hydrogen atom, a halogen atom, a hydroxyl, a $C_{1-3}$ alkoxy, a $C_{1-3}$ alkyl, a $C_{3-7}$ cycloalkyl, an O—C(O)—$C_{1-6}$ alkyl group, or $R_2$ and $R'_2$ together form an oxo group;

$R_3$ represents a hydrogen atom, a $C_{1-6}$ alkyl optionally substituted with a hydroxyl, a $C_{1-6}$ cycloalkyl or a $C_{1-3}$ alkoxy;

one or other of $R_4$ and $R_5$ represents a group Z

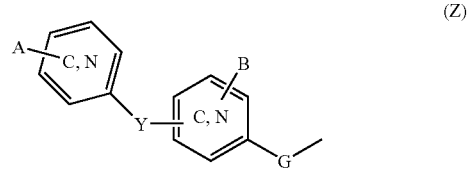

and one or other of $R_4$ and $R_5$ represents a group —C(X)$R_6$;

G represents a single bond or a —CH$_2$— group;

Y represents a single bond, an oxygen or sulfur atom, a $C_{1-4}$ alkylene group or —N(W)—, the —$C_{1-4}$ alkylene-group being optionally substituted with a hydroxyl or $C_{1-3}$ alkoxy group;

W represents either a hydrogen atom, a $C_{1-3}$ alkyl optionally substituted with a phenyl, or a phenyl;

A and B represent, independently of each other, a hydrogen or halogen atom, a hydroxyl, $C_{1-3}$ alkyl, $C_{1-3}$ alkoxy, trifluoromethyl, trifluoromethoxy or —O—CHF$_2$ group; on condition that if Y is a single bond or an oxygen atom and if the group Z is of the type

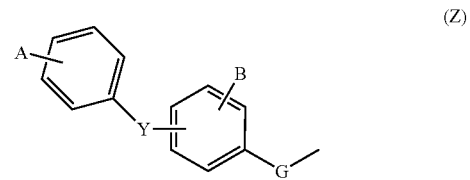

then A is other than a hydrogen atom;

X represents an oxygen atom or a sulfur atom;

$R_6$ represents a $C_{1-6}$ alkoxy, hydroxyl or —NR$_7$R$_8$ group;

the $C_{1-6}$ alkoxy group being optionally substituted with a phenyl;

$R_7$ and $R_8$ represent, independently of each other:

either a hydrogen atom; or a $C_{1-6}$ alkyl group optionally substituted with a $C_{3-7}$ cycloalkyl, a $C_{3-7}$ cycloalkenyl, a $C_{1-3}$ alkoxy, a phenyl, a morpholinyl or a pyridyl; or a $C_{3-7}$ cycloalkyl, $C_{1-6}$ alkoxy or phenyl group; the said $C_{3-7}$ cycloalkyl and phenyl groups being optionally substituted with one or two groups chosen from a halogen atom, a hydroxyl group, a $C_{1-3}$ alkyl and a $C_{1-3}$ alkoxy group; or $R_7$ and $R_8$, with the nitrogen atom that bears them, form an aziridine, azetidine, pyrrolidine, piperidine, morpholine or benzopiperidine ring.

DETAILED DESCRIPTION OF THE INVENTION

Among the compounds of general formula (I), a first subgroup of compounds consists of the compounds for which $R_1$ represents a $C_{1-6}$ alkyl or a phenyl optionally substituted with one to three halogen atoms.

Among the compounds of general formula (I), a second subgroup of compounds consists of the compounds for which $R_2$ and $R'_2$ represent, independently of each other, a hydrogen atom or a hydroxyl, or $R_2$ and $R'_2$ together form an oxo group.

Among the compounds of general formula (I), a third subgroup of compounds consists of the compounds for which $R_3$ represents a $C_{1-6}$ alkyl.

Among the compounds of general formula (I), a fourth subgroup of compounds consists of the compounds for which:

one or other of $R_4$ and $R_5$ represents a group Z

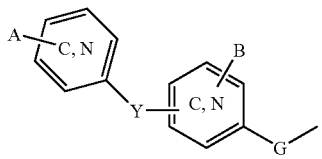

and one or other of $R_4$ and $R_5$ represents a group —C(X) $R_6$;

G represents a single bond;

Y represents a single bond, an oxygen or sulfur atom, or a $C_{1-4}$ alkylene group, more particularly methylene;

A and B represent, independently of each other, a hydrogen atom, a halogen atom, more particularly fluorine, or a trifluoromethyl or trifluoromethoxy group; on condition that if Y is a single bond or an oxygen atom and if the group Z is of the type

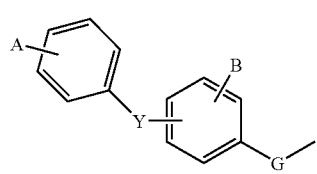

then A is other than a hydrogen atom;

X represents an oxygen atom or a sulfur atom;

$R_6$ represents a $C_{1-6}$ alkoxy group, more particularly a methoxy or an ethoxy.

The compounds for which A, B, W, X, Y, Z, $R_1$, $R_2$, $R'_2$, $R_3$, $R_4$, $R_5$, $R_6$, $R_7$ and $R_8$ are as defined in the subgroups of compounds above, form a fifth subgroup.

Among the compounds of general formula (I) and of the above subgroups, a sixth subgroup of compounds consists of the compounds for which:

$R_1$ represents a $C_{1-4}$ alkyl, preferably an isopropyl or a tert-butyl, or a phenyl substituted with two fluorine atoms; and/or $R_2$ represents a hydrogen atom or a hydroxyl and $R'_2$ represents a hydrogen atom; and/or $R_3$ represents a $C_{1-4}$ alkyl, preferably a methyl, ethyl or propyl; and/or X represents an oxygen atom.

In the context of the present invention, the following definitions apply:

$C_{t-z}$ in which t and z may take the values from 1 to 7, a carbon-based chain which may contain from t to z carbon atoms, for example $C_{1-3}$ a carbon-based chain which may contain from 1 to 3 carbon atoms, $C_{3-6}$ a carbon-based chain which may contain from 3 to 6 carbon atoms, etc.;

alkyl, a saturated, linear or branched aliphatic group; for example, a $C_{1-6}$ alkyl group represents a linear or branched carbon-based chain of 1 to 6 carbon atoms, more particularly a methyl, ethyl, propyl, isopropyl, butyl, isobutyl, sec-butyl, tert-butyl, etc., preferably a methyl, ethyl, propyl or isopropyl;

alkylene, a saturated, linear or branched divalent alkyl group, for example a $C_{1-3}$-alkylene group represents a linear or branched divalent carbon-based chain of 1 to 3 carbon atoms, more particularly a methylene, ethylene, isopropylene or propylene;

cycloalkyl, a cyclic alkyl group, for example a $C_{3-7}$ cycloalkyl represents a cyclic carbon-based chain of 3 to 7 carbon atoms, more particularly a cyclopropyl, cyclobutyl, cyclopentyl, cyclohexyl or cycloheptyl, preferably a cyclopentyl or cyclohexyl;

cycloalkenyl, a mono- or polyunsaturated cyclic alkyl group, for example a $C_{3-7}$ cycloalkenyl group represents a mono- or polyunsaturated cyclic carbon-based chain of 3 to 7 carbon atoms, more particularly a cyclopropenyl, cyclobutenyl, cyclopentenyl, cyclohexenyl or cycloheptenyl, preferably a cyclopentenyl or cyclohexenyl;

thioalkyl, an S-alkyl group containing a saturated, linear or branched aliphatic chain;

alkoxy, an —O-alkyl group containing a saturated, linear or branched aliphatic chain;

halogen atom, a fluorine, a chlorine, a bromine or an iodine;

"$R_2$ and $R'_2$ together form an oxo groups" the group such that:

and in the group Z, the aromatic group

is such that one of the carbon atoms of the aromatic ring may be replaced with a nitrogen atom in the position in which there is no substituent A or B.

The compounds of general formula (I) may comprise one or more asymmetric carbons. They may thus exist in the form of enantiomers or diastereoisomers. These enantiomers and diastereoisomers, and also mixtures thereof, including racemic mixtures, form part of the invention. When the carbon bearing $R_2$ and $R'_2$ and/or the carbon bearing $R_3$ are asymmetric, the preferred compounds are those of general formula (I) for which the carbon bearing $R_2$ and $R'_2$ is of (S) configuration and/or the carbon bearing $R_3$ is of (S) configuration.

The compounds of formula (I) may exist in the form of bases or of acid-addition salts. Such addition salts form part of the invention.

These salts are advantageously prepared with pharmaceutically acceptable acids, but the salts of other useful acids, for example for the purification or isolation of the compounds of formula (I), also form part of the invention.

The compounds of general formula (I) may be in the form of hydrates or solvates, i.e. in the form of associations or combinations with one or more water molecules or with a solvent. Such hydrates and solvates also form part of the invention.

A second subject of the present invention is processes for preparing the compounds of formula (I).

Thus, these compounds may be prepared via processes, illustrated in the schemes that follow, the operating conditions of which are standard for those skilled in the art.

The term "protecting group" means a group that prevents the reactivity of a function or position, during chemical reaction that could affect it, and which restores the molecule after cleavage according to methods known to those skilled in the art. Examples of protecting groups and protection and deprotection methods are given, inter alia, in *Protective groups in Organic Synthesis*, Greene et al., 2$^{nd}$ Ed. (John Wiley & Sons, Inc., New York).

The meanings of A, B, W, X, Y, Z, $R_1$, $R_2$, $R'_2$, $R_3$, $R_4$, $R_5$, $R_6$, $R_7$ and $R_8$ in the compounds of formulae (II) to (XVIII) below are as defined for the compounds of formula (I), unless another definition is specified.

According to scheme 1 below, the compound of formula (I) may be obtained by peptide coupling of the 2-aminothiazole of formula (III) with the acylamino acid of formula (II) according to conditions known to those skilled in the art, for example in the presence of benzotriazol-1-yloxytris(pyrrolidino)phosphonium hexafluorophosphate (PyBOP) or benzotriazol-1-yloxytris(dimethylamino)phosphonium hexafluorophosphate (BOP) and N-ethylmorpholine or N-methylmorpholine in an inert solvent such as N,N-dimethylformamide, acetonitrile or dichloromethane, at a temperature that can range from 0° C. to room temperature.

The compound of formula (II) may be obtained by peptide coupling of the compound of formula (IV) with the protected acid of formula (V), in which Pg represents a protecting group, for example a benzyl, according to methods known to those skilled in the art, as described above. The compound thus obtained is then deprotected. In the case where the protection is a benzyl, the compound is hydrogenated beforehand in the presence of palladium-on-charcoal in absolute ethanol under an atmospheric pressure of hydrogen, at room temperature, to give the compound of formula (II).

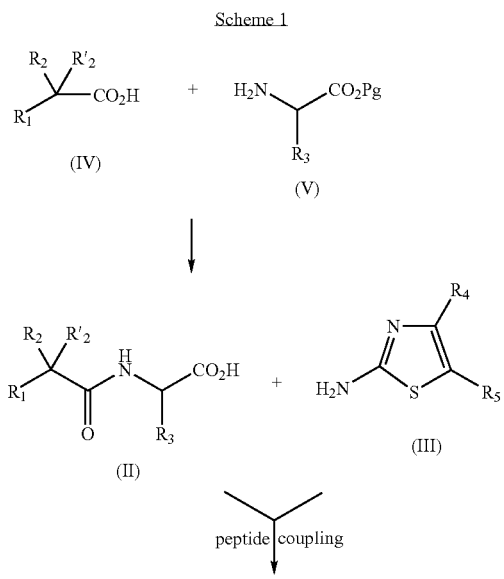

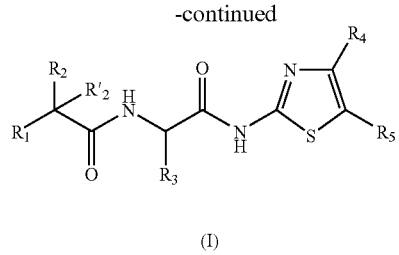

Alternatively, the compound of formula (I) may be prepared according to scheme 2.

According to scheme 2 below, the compound of formula (I) may be obtained by peptide coupling of the compound of formula (IV) with the amine of formula (VI), according to methods known to those skilled in the art, for instance in the presence of hydroxybenzotriazole hydrate (HOBt) and 1-ethyl-3-(3-dimethylaminopropyl)carbodiimide hydrochloride (EDAC HCl).

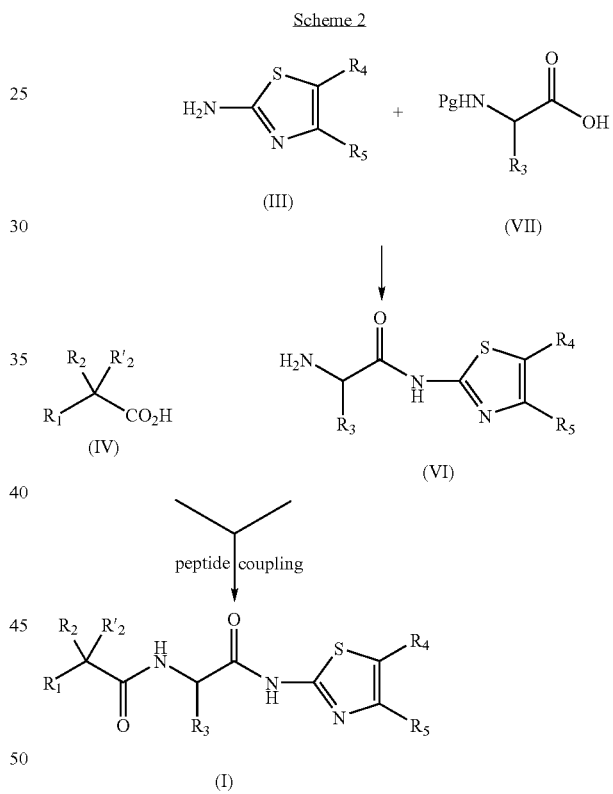

The compound of formula (VI) may be obtained by peptide coupling of the 2-aminothiazole of formula (III) with the protected amine of formula (VII) in which Pg represents a protecting group, for example an N-tert-butoxycarbonyl (Boc), according to methods known to those skilled in the art, as described above. The compound thus obtained is then deprotected. In the case where the protection is a Boc, the deprotection is performed by acidic hydrolysis, in the presence of gaseous hydrogen chloride dissolved in an anhydrous solvent, or of trifluoroacetic acid, to give the compound of formula (VI).

The compounds of formula (I) in which $R_2$ and $R'_2$ form an oxo group may be obtained by oxidation of a compound of formula (I) in which $R_2$ or $R'_2$ represents a hydroxyl group. The reaction may be performed according to the conditions known to those skilled in the art, for example with the Dess- Martin reagent. These compounds may also be obtained by direct coupling of a keto acid of formula (IV), in which $R_2$ and $R'_2$ together form an oxo group, with an amine of formula (VI) according to the conditions known to those skilled in the art. The methods for preparing such keto acids are known to those skilled in the art.

The compound of formula (III) in which $R_4$=—C(O)—$R_6$, $R_6$ representing a $C_{1-6}$ alkoxy group, may be obtained according to scheme 3 below.

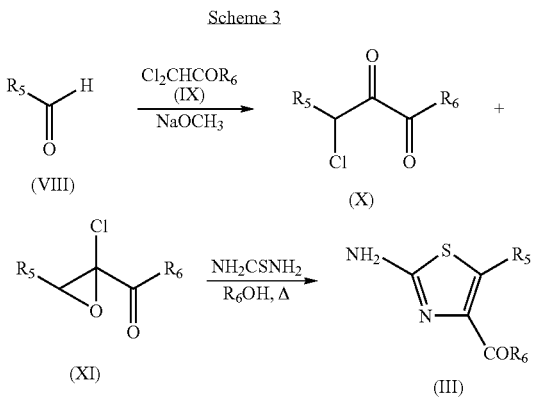

According to scheme 3, the compound of formula (III) may be obtained by reacting an aldehyde of formula (VIII) in which $R_5$ is as defined above with the methyldichloroacetate of formula (IX) in which $R_6$ represents a $C_{1-6}$ alkoxy optionally substituted with a phenyl, and, for example, sodium methoxide or ethoxide, at 0° C., according to an adaptation of the process described by Takeda (Bull. Chem. Soc. JP, 1970, p. 2997). The mixture of products (X) and (XI) obtained is treated with thiourea in the presence, for example, of methanol or ethanol at reflux temperatures for about 4 to 8 hours to give the compound of formula (III).

The compound of formula (III) in which $R_4$=—C(O)—$R_6$, $R_6$ representing a hydroxyl, may be obtained by hydrolysis of the above compounds for which $R_6$ represents a $C_{1-6}$ alkoxy group optionally substituted with a phenyl, according to the conditions known to those skilled in the art.

The compound of formula (III) in which $R_5$=—C(O)—$R_6$, $R_6$ representing a $C_{1-6}$ alkoxy group, may be obtained according to scheme 4 below.

According to scheme 4, the compound of formula (III) may be obtained by bromination of β-keto ester of formula (XIII), in which $R_6$ represents a $C_{1-6}$ alkoxy optionally substituted with a phenyl, to give the compound of formula (XII), followed by a reaction with thiourea, according to an adaptation of the process described by A. Barton et al. (J. C. S Perkin 1, 1982, p. 159).

The β-keto ester of formula (XIII) may be obtained by reacting a ketone of formula (XIV) with a dialkyl carbonate of formula (XVI) in which $R_6$ represents a $C_{1-6}$ alkoxy optionally substituted with a phenyl, according to an adaptation of the process described by L. Crombie et al. (J. C. S Perkin Trans I, 1987, p. 323). The β-keto ester of formula (XIII) may also be obtained by reacting an acid of formula (XV) activated with carbonyldiimidazole (CDI) with a malonate of formula (XVIa) in which $R_6$ represents a $C_{1-6}$ alkoxy optionally substituted with a phenyl, according to an adaptation of the process described, for example, by D. W. Brooks et al. (Angew. Chem. Int. Ed., 1979, p. 72).

The compound of formula (III) in which $R_5$=—C(O)—$R_6$, $R_6$ representing a hydroxyl, may be obtained by hydrolysis of the above compounds for which $R_6$ represents a $C_{1-6}$ alkoxy group, according to the conditions known to those skilled in the art.

The compound of formula (III) in which $R_4$ or $R_5$ represents a group —C(O)—$NR_7R_8$ may be obtained according to scheme 5.

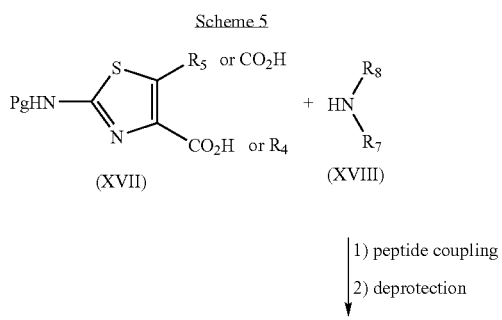

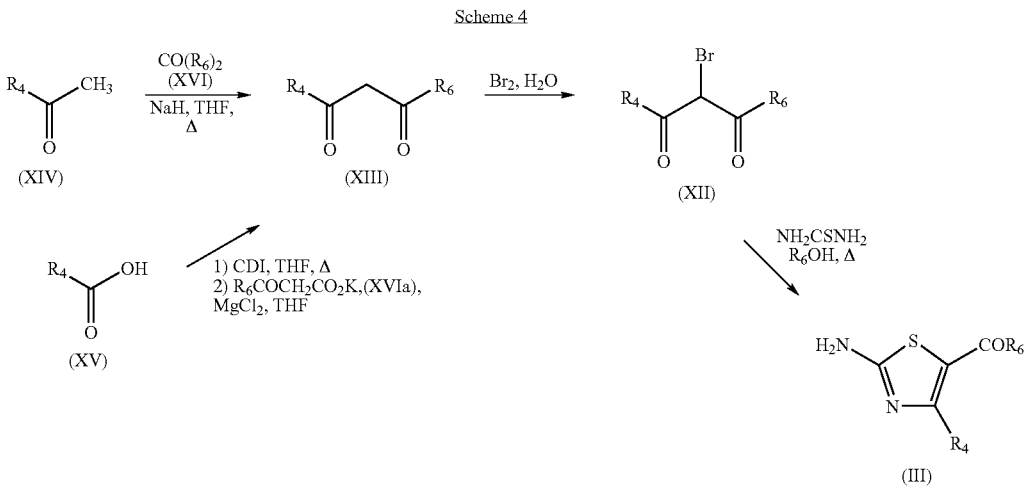

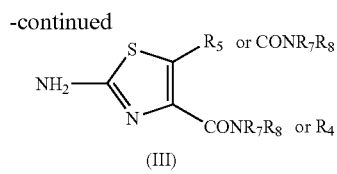

(III)

According to scheme 5, the compound of formula (III) is obtained by peptide coupling of the compound of formula (XVII), in which $R_5$ or $R_4$ represents a carboxylic group and Pg a protecting group such as a Boc, with a compound of formula (XVIII) in the presence, for example, of HOBt and (EDAC HCl). The compound thus obtained is then deprotected according to the conditions known to those skilled in the art. The compound of formula (XVII), in which Pg represents a Boc, may be obtained by protecting a compound of formula (III) in which $R_4$ or $R_5$ represents a group —C(O)$R_6$ and $R_6$ is a $C_{1-6}$ alkoxy optionally substituted with a phenyl, via the action of di-tert-butyl dicarbonate in anhydrous tetrahydrofuran in the presence of dimethylaminopyridine at room temperature, followed by hydrolysis of the carboxylate under the conditions known to those skilled in the art, for example with lithium hydroxide in a 7/3 (v/v) tetrahydrofuran/water mixture at a temperature of 60° C.

The compounds of general formula (I), in which $R_4$ or $R_5$ represents a group —C(X)$R_6$ and X=S, may be prepared from corresponding compounds of general formula (I) or (III), in which $R_4$ or $R_5$ represents a group —C(X)$R_6$ and X=O, by conversion of the C(O) group into a C(S) group, for example using Lawesson's reagent according to a method similar to that described by M. P. Cava et al. in Tetrahedron 1985, p. 5061.

In schemes 1 to 5, the starting compounds and the reagents, especially the compounds of formula (III), (IV), (V), (VII), (VIII), (IX), (XIV), (XV), (XVI), (XVIa), (XVII) and (XVIII), when their mode of preparation is not described, are commercially available or described in the literature, or may be prepared via methods described therein or known to those skilled in the art.

For example, the compounds of formula (IV) in which $R_2$ or $R'_2$ represents a hydroxyl may be prepared by addition of trimethylsilyl cyanide to an aldehyde according to an adaptation of the process described by D. A. Evans et al. (J. C. S., Chem. Comm. 1973, p. 55) or via the action of sodium nitrite on an α-amino acid according to an adaptation of the process described by I. Shinn et al. (J. Org. Chem., 2000, p. 7667).

For example, the compounds of formula (XV) in which Y=O may be prepared according to an adaptation of the process described by Sindel et al. (Collect. csech. chim. Tchecosl., 1982, p. 72) or by Atkinson et al. (J. Med. Chem., 1983, p. 1353).

For example, the compounds of formula (XV) in which Y is of the —$C_{1-4}$ alkylene-type may be prepared, for example, according to an adaptation of the process described by Crow et al. (Austral. J. Chem., 1981, p. 1037) or alternatively via a Suzuki reaction according to an adaptation of the process described by Chahen et al. (Synlett, 2003, p. 1668).

For example, the compounds of formula (XV) in which Y=S may be prepared according to the process described by Goldberg (Chem. Ber., 1994, p. 4526).

For example, the compounds of formula (XV) in which Y=N(W) may be prepared according to the process described by Chane et al. (Tetrahedron Letters, 1998, p. 2933) or Chamain (Tetrahedron Letters, 1998, p. 4179) or Huwe et al. (Tetrahedron Letters, 1999, p. 683).

For example, the compounds of formula (XV) in which Y is a single bond may be prepared via a Suzuki reaction according to the conditions known to those skilled in the art, for example according to the process described by Deng et al., Synthesis, 2003, p. 337 or Meier et al., Synthesis, 2003, p. 551.

For example, the compounds of formula (VIII) may be obtained by reduction of the compounds of formula (XV) according to the conditions known to those skilled in the art.

When a function of a compound is reactive, for example when $R_1$ comprises a hydroxyl, it may be necessary to protect it before reaction. A person skilled in the art can readily determine the need for prior protection.

The examples that follow describe the preparation of certain compounds in accordance with the invention. These compounds are not limiting and serve merely to illustrate the invention.

The numbers of the compounds given as examples refer to those given in the table hereinbelow. The elemental microanalyses and the NMR, IR or LC-MS (liquid chromatography coupled to mass spectrometry) analyses confirm the structures of the compounds obtained.

Example 1

Methyl 2-{2-(S)-[2-(3,5-difluorophenyl)acetylamino]-pentanoyl}amino-5-[2-(4-fluorophenoxy)phenyl]thiazole-4-carboxylate (Compound 13)

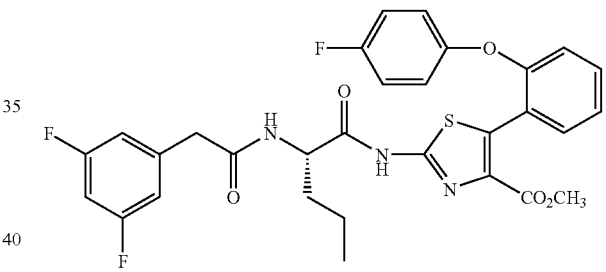

Example 1.1

2-(4-Fluorophenoxy)benzoic acid

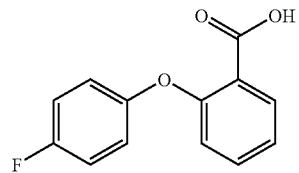

100 g of potassium carbonate are added slowly to a mixture of 120 g of 2-iodobenzoic acid, 1 g of copper powder and 54.4 g of 4-fluorophenol in 200 ml of N,N-dimethylformamide. The mixture is heated at 160° C. for 4 hours and is then allowed to cool before evaporating. The residue is taken up in distilled water, acidified with aqueous 1N hydrochloric acid solution and then extracted with ethyl acetate. The organic phase is washed with saturated sodium chloride solution, dried over anhydrous sodium sulfate and then concentrated. The desired product crystallizes from a diethyl ether/pentane mixture. 50 g of a white solid are obtained.

LC/MS: MH$^+$=233

Example 1.2

2-(4-Fluorophenoxy)-O,N-dimethylbenzamide

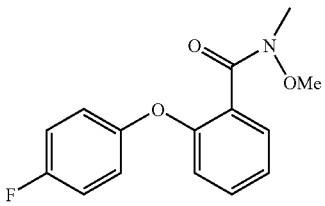

29.7 g of hydroxybenzotriazole hydrate are added to a solution of 50 g of 2-(4-fluorophenoxy)benzoic acid, obtained in step 1.1, in 450 ml of N,N-dimethylformamide, followed by addition of 37 g of (EDAC HCl), 19 g of (O,N-dimethylhydroxylamine HCl) and 19.4 g of N-methylmorpholine. The mixture is stirred at room temperature for 16 hours. The solvent is evaporated off, the residue is taken up in ethyl acetate and the organic phase is washed twice with saturated aqueous sodium chloride solution, once with distilled water, once with aqueous 1M potassium hydrogen sulfate solution and then with saturated aqueous sodium chloride solution. The resulting solution is dried over anhydrous sodium sulfate and then concentrated. 49 g of a colored oil are obtained, and are used without further purification in the following synthesis.

LC/MS: MH$^+$=276

Example 1.3

2-(4-Fluorophenoxy)benzaldehyde

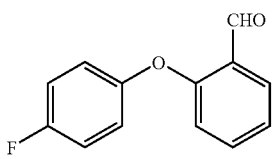

48.5 g of 2-(4-fluorophenoxy)-O,N-dimethylbenzamide, obtained in step 1.2, in 300 ml of anhydrous tetrahydrofuran are added dropwise to 100 ml of a 1M solution of lithium aluminum hydride in tetrahydrofuran at 0° C. The mixture is stirred at 0° C. for 1 hour and then hydrolyzed dropwise with 40 ml of aqueous 1M potassium hydrogen sulfate solution. The resulting mixture is evaporated and the residue is taken up in ethyl acetate and washed twice with aqueous 1M potassium hydrogen sulfate solution and then with saturated aqueous sodium chloride solution. The resulting solution is dried over anhydrous sodium sulfate and then concentrated. 35 g of a colored oil are obtained.

LC/MS: MH$^+$=217

NMR 300 MHz (CDCl$_3$) δ ppm: 6.70-7.00 (m, 4H); 7.20-7.35 (m, 2H); 7.55 (t, 1H); 7.95 (d, 1H); 10.43 (s, 1H).

Example 1.4

Methyl 2-amino-5-[2-(4-fluorophenoxy)-phenyl]thiazole-4-carboxylate

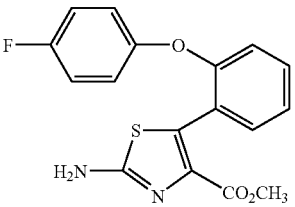

30 g of methyl dichloroacetate are added, at 0° C., to 35 g of 2-(4-fluorophenoxy)benzaldehyde, obtained in step 1.3, dissolved in 400 ml of diethyl ether, followed by dropwise addition of 325 ml of a solution (0.5 M) of sodium methoxide in methanol. After 1 hour at 0° C., only diethyl ether is evaporated off, while retaining the methanol, 11 g of thiourea are added and the mixture is refluxed for 6 hours. The reaction medium is evaporated to dryness and the residue is taken up in ethyl acetate and washed with aqueous 10% ammonium hydroxide solution and then with saturated aqueous sodium chloride solution. The organic phase is dried over anhydrous sodium sulfate and then concentrated. The residue is taken up in 100 ml of diethyl ether and filtered through a sinter funnel. 30 g of a white solid are obtained.

LC/MS: MH$^+$=345

NMR 300 MHz (CDCl$_3$) δ ppm: 3.70 (s, 3H); 5.55 (broad s, 2H); 6.55-6.80 (m, 4H); 7.00 (d, 1H); 7.20 (t, 1H); 7.35-7.45 (m, 2H).

Example 1.5

Methyl 2-[2-(S)-pentanoylamino]amino-5-[2-(4-fluorophenoxy)phenyl]thiazole-4-carboxylate

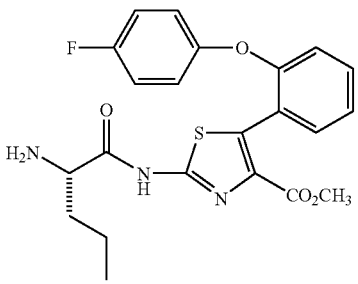

2.75 g of N-methylmorpholine, 14.30 g of PyBOP and then 5.97 g of (S)-BocNorvaline are added to 8.6 g of methyl 2-amino-5-[2-(4-fluorophenoxy)phenyl]-thiazole-4-carboxylate, obtained in step 1.4, dissolved in 200 ml of N,N-dimethylformamide at 0° C. The reaction medium is allowed to return to room temperature and is then stirred for 16 hours. After evaporation, the residue is taken up in ethyl acetate and washed twice with saturated aqueous sodium bicarbonate solution, twice with water, once with aqueous 1M potassium hydrogen sulfate solution and then with saturated aqueous sodium chloride solution. The organic phase is dried over anhydrous sodium sulfate and then concentrated. The residue is chromatographed on a column of silica gel, eluting with a 3/7 (v/v) mixture of ethyl acetate and petroleum ether. 8.5 g of a white solid are obtained.

LC/MS: MH+=544

NMR 300 MHz (CDCl₃) δ ppm: 0.88 (t, 3H); 1.38 (s, 9H); 1.39-1.55 (2 m, 2H); 1.75 (m, 2H); 3.35 (broad s, 1H); 3.68 (s, 3H); 4.28 (m, 1H); 5.65 (d, 1H); 6.80-6.90 (m, 5H); 7.10 (t, 1H); 7.20-7.32 (m, 2H).

6.5 g of product obtained above is then deprotected by dissolving in 60 ml of trifluoroacetic acid and stirred at room temperature for 30 minutes, and the solution is then evaporated. The residue is taken up in ethyl acetate and washed twice with saturated aqueous sodium carbonate solution, and then with saturated aqueous sodium chloride solution. The organic phase is dried over anhydrous sodium sulfate and then evaporated to give 3.9 g of a white solid.

LC/MS: MH+=444

Example 1.6

Methyl 2-{2-(S)-[2-(3,5-difluorophenyl)acety-lamino]-pentanoyl}amino-5-[2-(4-fluorophenoxy)phenyl]thiazole-4-carboxylate 0.20 g of N-methylmorpholine, 0.99 g of PyBOP and then 0.33 g of 3,5-difluorophenylacetic acid are added to 0.7 g of methyl 2-amino-2-[2-(S)-pentanoylamino]-5-[2-(4-fluorophenoxy)phenyl]thiazole-4-carboxylate, obtained in Example 1.5, dissolved in 30 ml of N,N-dimethylformamide at 0° C. The mixture is allowed to warm to room temperature and is stirred for 18 hours. The reaction medium is evaporated. The residue is taken up in ethyl acetate and washed twice with saturated aqueous sodium bicarbonate solution, twice with water, once with aqueous 1M potassium hydrogensulfate solution, and then with saturated aqueous sodium chloride solution. The organic phase is dried over anhydrous sodium sulfate and then concentrated. The residue is chromatographed on a column of silica, eluting with a 1/1 (v/v) petroleum ether/ethyl acetate mixture to give 0.56 g of a white solid.

LC/MS: MH+=558

NMR described in the table (compound 13)

Example 2

Methyl 2-{2-(S)-[2-(S)-hydroxy-(3,3-dimethyl)butyryl-amino]pentanoyl}amino-5-[2-(phenylthio)-3-pyridyl]-thiazole-4-carboxylate (Compound 19)

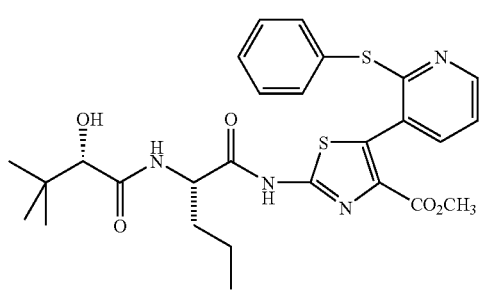

Example 2.1

(2-Phenylthio)-O,N-dimethylnicotinamide

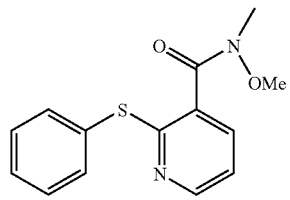

(2-Phenylthio)-O,N-dimethylnicotinamide may be obtained according to a method similar to that described in step 1.2 of Example 1. Starting with 20 g of 2-phenylthionicotinic acid, 21.9 g of a colorless oil are obtained, and are used without further purification in the following synthesis.

LC/MS: MH+=275

NMR 300 MHz (CDCl₃) δ ppm: 3.35 (broad s, 3H); 3.58 (broad s, 3H); 7.35 (m, 3H); 7.50 (m, 2H); 7.60 (d, 2H); 8.40 (d, 1H)

Example 2.2

(2-Phenylthio)nicotinaldehyde

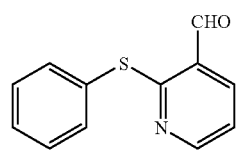

(2-Phenylthio)nicotinaldehyde may be obtained according to a method similar to that described in step 1.3 of Example 1. Starting with 21.9 g of (2-phenyl-thio)-O,N-dimethylnicotinamide (Weinreb amide), obtained in step 2.1, and 48 ml of a 1M solution of lithium aluminum hydride in 300 ml of tetrahydrofuran, 16.6 g of a white solid are obtained.

NMR 300 MHz (CDCl₃) δ ppm: 7.18 (m, 1H); 7.42 (m, 3H); 7.57 (m, 2H); 8.05 (d, 1H); 8.46 (d, 1H); 10.35 (s, 1H).

Example 2.3

Methyl 2-amino-5-[2-phenylthio)-3-pyridyl]thiazole-4-carboxylate

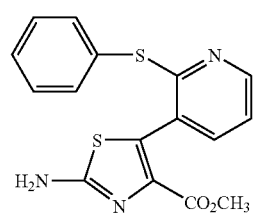

Methyl 2-amino-5-[2-(phenylthio)-3-pyridyl]thiazole-4-carboxylate may be obtained according to a method similar to that described in step 1.4 of Example 1. Starting with 16.5 g of (2-phenylthio)nicotinaldehyde obtained in step 2.2, 11.2 g of methyl dichloroacetate and 150 ml of 0.5M sodium methoxide in 300 ml of diethyl ether, 19 g of a pale yellow solid are obtained.

LC/MS: MH$^+$=344

NMR 300 MHz (DMSOd$_6$) δ ppm: 3.41 (broad s, 2H); 3.60 (s, 3H); 7.20 (broad d, 1H); 7.38-7.48 (m, 5H); 7.65 (broad d, 1H); 8.30 (broad d, 1H).

Example 2.4

Methyl 2-[2-(S)-pentanoylamino]amino-5-[2-(phenylthio)-3-pyridyl]thiazole-4-carboxylate

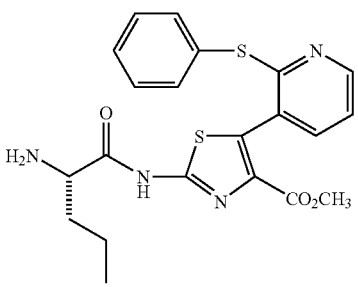

Methyl 2-[2-(S)-pentanoylamino]amino-5-[2-(phenylthio)-3-pyridyl]thiazole-4-carboxylate may be obtained according to a method similar to that described in step 1.5 of Example 1. Starting with 5.14 g of methyl 2-amino-5-[2-phenylthio)-3-pyridyl]thiazole-4-carboxylate, obtained in Example 2.3, and 3.58 g of (S)-BocNorvaline, in the presence of 8.58 g of PyBOP and 1.66 g of N-methylmorpholine in N,N-dimethylformamide at 0° C., and after chromatography, 3.5 g of a pale yellow solid are obtained.

LC/MS: MH$^+$=542

NMR 300 MHz (DMSOd$_6$) δ ppm: 0.87 (t, 3H); 1.45 (s, 9H); 1.70 (m, 2H); 1.97 (m, 2H); 3.72 (s, 3H); 4.45 (m, 1H); 5.23 (m, 1H); 7.10 (m, 1H); 7.30 (m, 3H); 7.42 (m, 2H); 7.50 (d, 1H); 8.39 (d, 1H).

3.5 g of the amine obtained above is then deprotected by dissolving in 150 ml of a solution of 4M hydrochloric acid in 1,4-dioxane and 20 ml of methanol. The mixture is stirred for 1 hour 30 minutes at room temperature and then evaporated. 3.2 g of a pale yellow solid are obtained.

LC/MS: MH$^+$=442

Example 2.5

Methyl 2-{2-(S)-[2-(S)-hydroxy-(3,3-dimethyl)butyryl-amino]pentanoyl}amino-5-[2-(phenylthio)-3-pyridyl]-thiazole-4-carboxylate Methyl 2-{2-(S)-[2-(S)-hydroxy-(3,3-dimethyl)butyrylamino]pentanoyl}amino-5-[2-(phenylthio)-3-pyridyl]thiazole-4-carboxylate may be obtained according to a method similar to that described in step 1.6 of Example 1. Starting with 0.9 g of methyl 2-[2-(S)-pentanoylamino]amino-5-[2-(phenylthio)-3-pyridyl]thiazole-4-carboxylate, obtained in step 2.4, and 0.25 g of (S)-2-hydroxy-3,3-dimethylbutyric acid, in the presence of 1 g of PyBOP and 0.59 g of N-methylmorpholine in 90 ml of N,N-dimethylformamide at 0° C., and after chromatography on a column of silica gel eluted with a 7/3 (v/v) ethyl acetate/petroleum ether mixture, 0.5 g of a white powder is obtained.

LC/MS: MH$^+$=557

NMR described in the table (compound 19)

Example 3

Methyl 2-{2-(S)-[2-(3,5-difluorophenyl)acetylamino]-pentanoyl}amino-5-[2-(4'-trifluoromethyl)biphenyl]-thiazole-4-carboxylate (Compound 5)

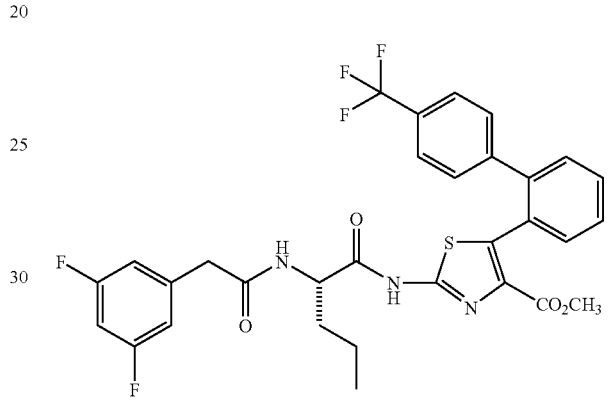

Example 3.1

Methyl 2-amino-5-[2-(4'-trifluoromethyl)-biphenyl]thiazole-4-carboxylate

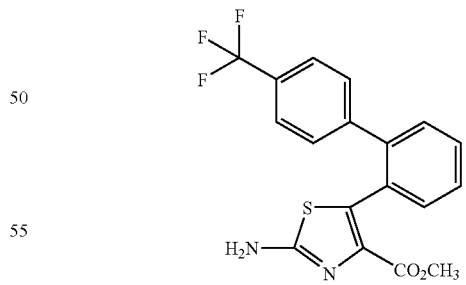

Methyl 2-amino-5-[2-(4'-trifluoromethyl)-biphenyl]thiazole-4-carboxylate may be obtained according to a method similar to that described in steps 1.2 to 1.4 of Example 1, starting with 26.6 g of 4-trifluoromethyl-2-biphenylcarboxylic acid. The Weinreb amide of this acid (28.2 g) is reduced to the aldehyde with lithium aluminum hydride to give 18.7 g of a pale yellow oil. The aldehyde (18 g) is reacted with 10.3 g of methyl dichloroacetate in the presence of 144 ml of 0.5M sodium methoxide, followed by 4.7 g of thiourea in refluxing methanol. 16 g of a pale yellow solid are obtained.

LC/MS: MH$^+$=379

Example 3.2

Methyl 2-[2-(S)-pentanoylamino]amino-5-[2-(4'-trifluoromethyl)biphenyl]thiazole-4-carboxylate

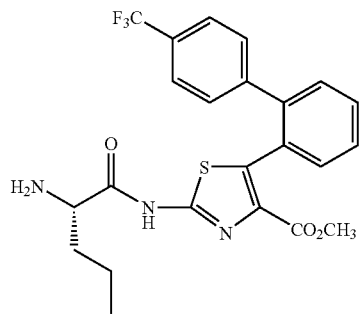

Methyl 2-[2-(S)-pentanoylamino]amino-5-[2-(4'-trifluoromethyl)biphenyl]thiazole-4-carboxylate may be obtained according to a method similar to that described in step 1.5 of Example 1. Starting with 2.26 g of methyl 2-amino-5-[2-(4'-trifluoromethyl)-biphenyl]thiazole-4-carboxylate, obtained in Example 3.1, and 1.43 g of (S)-BocNorvaline, in the presence of 3.43 g of PyBOP and 0.66 g of N-methylmorpholine in 120 ml of N,N-dimethylformamide at 0° C., and after chromatography on a column of silica gel eluted with 8/2 (v/v) petroleum ether/ethyl acetate, 2 g of a pale yellow solid are obtained.

LC/MS: MH$^+$=578

NMR 300 MHz (CDCl$_3$) δ ppm: 0.92 (t, 3H); 1.45 (s, 9H); 1.70 (m, 2H); 1.80 (m, 2H); 3.69 (s, 3H); 4.40 (m, 1H); 5.10 (m, 1H); 6.98 (m, 4H); 7.27 (m, 2H); 7.32 (d, 2H).

The compound obtained is then deprotected with 50 ml of trifluoroacetic acid according to the process described in Example 1.5. 1 g of a white foam is obtained.

LC/MS: MH$^+$=478

Example 3.3

Methyl 2-{2-(S)-[2-(3,5-difluorophenyl)-acetylamino]pentanoyl}amino-5-[2-(4'-trifluoromethyl)-biphenyl]thiazole-4-carboxylate Methyl 2-{2-(S)-[2-(3,5-difluoro-phenyl)acetylamino]pentanoyl}amino-5-[2-(4'-trifluoro-methyl)biphenyl]thiazole-4-carboxylate may be obtained according to a method similar to that described in step 1.6 of Example 1. Starting with 0.94 g of methyl 2-[2-(S)-pentanoylamino]amino-5-[2-(4'-trifluoro-methyl)biphenyl]thiazole-4-carboxylate, obtained in step 3.2, and 0.18 g of 3,5-difluorophenylacetic acid, in the presence of 0.55 g of PyBOP and 0.11 g of N-methylmorpholine in 50 ml of N,N-dimethylformamide at 0° C., and after chromatography on silica gel eluted with a 7/3 (v/v) ethyl acetate/petroleum ether mixture, 0.45 g of a white powder is obtained.

LC/MS: MH$^+$=632

NMR described in the table (compound 5)

The table that follows illustrates the chemical structures and the physical properties of a number of examples of compounds according to the invention.

| N° | R₁ | R₂, R'₂ | R₃ | R₄ | R₅ | R₆ | R₇,R₈ | NMR (DMSO-d6 when not specified) |
|---|---|---|---|---|---|---|---|---|
| 1. | (CH₃)₃C— | OH, H(S) | CH₃(CH₂)₂— (S) | —COR₆ | 4-CF₃-biphenyl-2-yl (2-methyl biphenyl with 4'-CF₃) | OCH₃ | — | 0.90(t, 3H); 0.93(s, 9H); 1.28-1.38(m, 2H); 1.73(m, 2H); 3.53(s, 3H); 3.59(d, 1H); 4.56(m, 1H); 5.63(d, 1H); 7.40(d, 2H); 7.54(m, 3H); 7.60(m, 1H); 7.70(d, 2H); 7.86(d, 1H); 12.58(broad s, 1H)*** |
| 2. | (CH₃)₃C— | OH, H(S) | CH₃(CH₂)₂— (S) | —COR₆ | 2-benzylphenyl | OCH₃ | — | 0.86(t, 3H); 0.89(s, 9H); 1.25-1.32(m, 2H); 1.69(m, 2H); 3.53(s, 3H); 3.54(d, 1H); 3.82(s, 2H); 4.52(m, 1H); 5.58(d, 1H); 6.90(d, 2H); 7.11(t, 1H); 7.16(m, 2H); 7.22 (m, 3H); 7.36(m, 1H); 7.80(d, 1H); 12.59 (s, 1H)*** |
| 3. | 3,5-difluorophenyl | OH, H(S) | CH₃(CH₂)₂— (S) | —COR₆ | 2-benzylphenyl | OCH₃ | — | 0.81(t, 3H); 1.22(m, 2H); 1.71(m, 2H); 3.53(s, 3H); 3.53(s, 2H); 6.54(d, 1H); 6.90(d, 2H); 7.07-7.37(3m, 10H); 8.27(d, 1H); 12.64 (broad s, 1H)*** |
| 4. | 3,5-difluorophenyl | OH, H(R) | CH₃(CH₂)₂— (S) | —COR₆ | 2-benzylphenyl | OCH₃ | — | 0.83(t, 3H); 1.25(m, 2H); 1.72(m, 2H); 3.53(s, 3H); 3.81(s, 2H); 4.44(m, 1H); 5.07(d, 1H); 6.41(d, 1H); 6.87(d, 2H); 7.07-7.35(4m, 10H); 8.30(d, 1H); 12.69 (broad s, 1H)*** |
| 5. | 3,5-difluorophenyl | H, H | CH₃(CH₂)₂— (S) | —COR₆ | 4-CF₃-biphenyl-2-yl | OCH₃ | — | 0.92(t, 3H); 1.30-1.41(m, 2H); 1.68(m, 2H); 3.58(s, 3H); 3.73(m, 2H); 4.46(m, 1H); 7.04(d, 2H); 7.14(t, 1H); 7.43(d, 2H); 7.53 (t, 3H); 7.56 (m, 1H); 7.72 (d, 2H); 8.56 (d, 1H); 12.72(broad s, 1H)*** |

-continued (I)

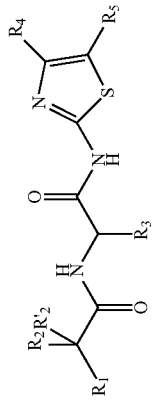

| N° | R₁ | R₂, R'₂ | R₃ | R₄ | R₅ | R₆ | R₇,R₈ | |
|---|---|---|---|---|---|---|---|---|
| 6. | 3,5-difluorophenyl | OH, H(S) | CH₃(CH₂)₂— (S) | —COR₆ | 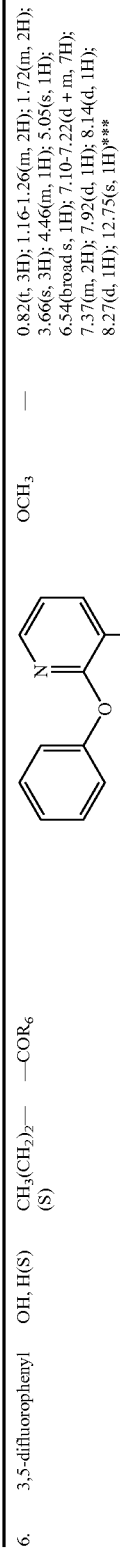 | OCH₃ | — | 0.82(t, 3H); 1.16-1.26(m, 2H); 1.72(m, 2H); 3.66(s, 3H); 4.46(m, 1H); 5.05(s, 1H); 6.54(broad s, 1H); 7.10-7.22(d + m, 7H); 7.37(m, 2H); 7.92(d, 1H); 8.14(d, 1H); 8.27(d, 1H); 12.75(s, 1H)*** |
| 7. | (CH₃)₃C— | OH, H(S) | CH₃(CH₂)₂— (S) | —COR₆ | 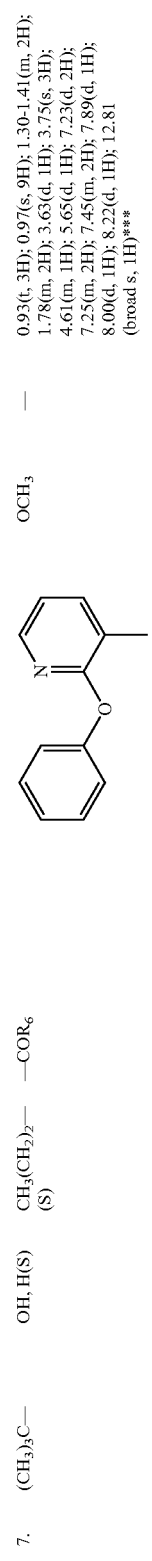 | OCH₃ | — | 0.93(t, 3H); 0.97(s, 9H); 1.30-1.41(m, 2H); 1.78(m, 2H); 3.63(d, 1H); 3.75(s, 3H); 4.61(m, 1H); 5.65(d, 1H); 7.23(d, 2H); 7.25(m, 2H); 7.45(m, 2H); 7.89(d, 1H); 8.00(d, 1H); 8.22(d, 1H); 12.81 (broad s, 1H)*** |
| 8. | 3,5-difluorophenyl | OH, H | CH₃(CH₂)₂— (S) | —COR₆ | 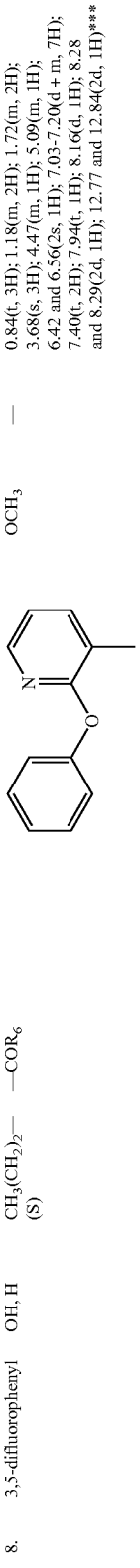 | OCH₃ | — | 0.84(t, 3H); 1.18(m, 2H); 1.72(m, 2H); 3.68(s, 3H); 4.47(m, 1H); 5.09(m, 1H); 6.42 and 6.56(2s, 1H); 7.03-7.20(d + m, 7H); 7.40(t, 2H); 7.94(t, 1H); 8.16(d, 1H); 8.28 and 8.29(2d, 1H); 12.77 and 12.84(2d, 1H)*** |
| 9. | 3,5-difluorophenyl | OH, H(S) | CH₃(CH₂)₂— (S) | —COR₆ | 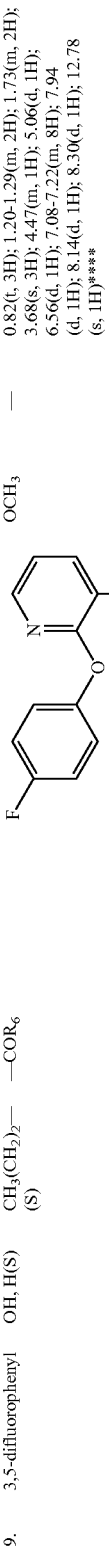 | OCH₃ | — | 0.82(t, 3H); 1.20-1.29(m, 2H); 1.73(m, 2H); 3.68(s, 3H); 4.47(m, 1H); 5.06(d, 1H); 6.56(d, 1H); 7.08-7.22(m, 8H); 7.94 (d, 1H); 8.14(d, 1H); 8.30(d, 1H); 12.78 (s, 1H)**** |
| 10. | 3,5-difluorophenyl | OH, H | CH₃(CH₂)₂— (S) | —COR₆ | 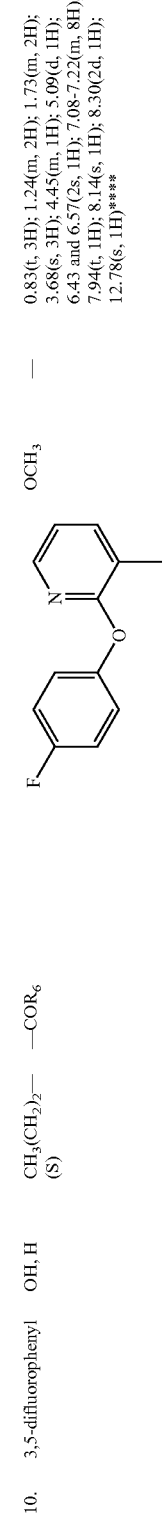 | OCH₃ | — | 0.83(t, 3H); 1.24(m, 2H); 1.73(m, 2H); 3.68(s, 3H); 4.45(m, 1H); 5.09(m, 1H); 6.43 and 6.57(2s, 1H); 7.08-7.22(m, 8H); 7.94(t, 1H); 8.14(s, 1H); 8.30(2d, 1H); 12.78(s, 1H)*** |

-continued (I)

| N° | R₁ | R₂,R'₂ | R₃ | R₄ | R₅ | | R₆ | R₇,R₈ | |
|----|----|----|----|----|----|----|----|----|----|
| 11. | (CH₃)₃C— | OH, H(S) | CH₃(CH₂)₂— (S) | —COR₆ | F | 3-methyl-2-(4-fluorophenoxy)pyridine | OCH₃ | — | 0.87(t, 3H); 0.89(s, 9H); 1.27-1.36(m, 2H); 1.73(m, 2H); 3.55(d, 1H); 3.68(s, 3H); 4.53(m, 1H); 5.59(d, 1H); 7.07(m, 2H); 7.22(m, 2H); 7.84(d, 1H); 7.94(d, 1H); 8.14(s, 1H)**** |
| 12. | 3,5-difluorophenyl | OH, H(S) | CH₃(CH₂)₂— (S) | —COR₆ | F | 2-methyl-(4-fluorophenoxy)benzene | OCH₃ | — | 0.82(t, 3H); 1.17-1.28(m, 2H); 1.72(m, 2H); 3.65(d, 1H); 3.63(s, 3H); 4.45(m, 1H); 5.06(d, 1H); 6.56(d, 2H); 6.93(m, 3H); 7.13-7.23(d, 1H); 7.94(m, 6H); 7.47(d, 1H); 7.49(d, 1H); 8.29(d, 1H); 12.66(s, 1H)**** |
| 13. | 3,5-difluorophenyl | H, H | CH₃(CH₂)₂— (S) | —COR₆ | F | 2-methyl-(4-fluorophenoxy)benzene | OCH₃ | — | 0.86(t, 3H); 1.27(m, 2H); 1.66(m, 2H); 3.55(m, 2H); 3.64(s, 3H); 4.41(m, 1H); 6.90(t, 2H); 6.93(d, 2H); 7.14(t, 1H); 7.21-7.25(d, 1H); 7.47(t, 1H); 7.48(d, 1H); 8.51(s, 1H)**** |
| 14. | (CH₃)₃C— | OH, H(S) | CH₃(CH₂)₂— (S) | —COR₆ | F | 2-methyl-(4-fluorophenoxy)benzene | OCH₃ | — | 0.86(t, 3H); 0.90(s, 9H); 1.25-1.35(m, 2H); 1.70(m, 2H); 3.55(d, 1H); 3.65(s, 3H); 4.52(m, 1H); 5.59(d, 1H); 6.91(m, 3H); 7.15-7.22(m, 3H); 7.42(t, 1H); 7.47(d, 1H); 7.82(d, 1H); 12.61(s, 1H)**** |
| 15. | 3,5-difluorophenyl | H,H | CH₃(CH₂)₂— (S) | —COR₆ | F | 2-methyl-(3-fluorophenoxy)benzene | OCH₃ | — | 0.83(t, 3H); 1.25-1.33(2m, 2H); 1.62(m, 2H); 3.55(m, 2H); 3.62(s, 3H); 4.39(m, 1H); 6.66(d, 2H); 6.87(t, 1H); 6.96(d, 2H); 7.07(d, 2H); 7.27(m, 2H); 7.48(m, 2H); 8.50(d, 1H); 12.68(s, 1H)**** |

-continued (I)

| Nº | $R_1$ | $R_2, R'_2$ | $R_3$ | $R_4$ | $R_5$ | $R_6$ | $R_7, R_8$ | |
|---|---|---|---|---|---|---|---|---|
| 16. | $(CH_3)_3C-$ | OH, H(S) | $CH_3(CH_2)_2-$ (S) | $-COR_6$ | 3,5-difluorophenyl (2-methylphenyl-O-3-fluorophenyl) | $OCH_3$ | — | 0.85(t, 3H); 0.88(s, 9H); 1.21-1.31(m, 2H); 1.69(m, 2H); 3.53(d, 1H); 3.62(s, 3H); 4.50(m, 1H); 5.57(d, 1H); 6.66(d, 2H); 6.87(t, 1H); 7.08(d, 1H); 7.30(m, 2H); 7.47(m, 2H); 7.08(d, 1H); 12.58 (s, 1H)**** |
| 17. | 3,5-difluorophenyl | OH, H(S) | $CH_3(CH_2)_2-$ (S) | $-COR_6$ | (2-methylphenyl-O-3-fluorophenyl) | $OCH_3$ | — | 0.79(t, 3H); 1.14-1.325(2m, 2H); 1.70(m, 2H); 3.55(m, 2H); 3.62(s, 3H); 4.42(m, 1H); 5.05(d, 1H); 6.53(s, 1H); 6.66(d, 2H); 6.88(t, 1H); 7.11(m, 4H); 7.27(m, 2H); 7.49(m, 2H); 8.26(d, 1H); 12.63(s, 1H)**** |
| 18. | 3,5-difluorophenyl | H, H | $CH_3(CH_2)_2-$ (S) | $-COR_6$ | (3-methylpyridin-2-yl-S-phenyl) | $OCH_3$ | — | 0.88(t, 3H); 1.31(m, 2H); 1.68(m, 2H); 3.56(m, 2H); 3.66(s, 3H); 4.44(m, 1H); 6.99(d, 2H); 7.06(t, 1H); 7.26(d, 2H); 7.38(m, 4H); 7.75(d, 1H); 8.38(d, 1H); 8.54(broad s, 1H)**** |
| 19. | $(CH_3)_3C-$ | OH, H(S) | $CH_3(CH_2)_2-$ (S) | $-COR_6$ | (3-methylpyridin-2-yl-S-phenyl) | $OCH_3$ | — | 0.87(t, 3H); 0.91(s, 9H); 1.27-1.37(m, 2H); 1.73(m, 2H); 3.57(d, 1H); 3.66(s, 3H); 4.57(m, 1H); 5.57(d, 1H); 7.27(d, 1H); 7.36(s, 4H); 7.75(d, 1H); 7.84(d, 1H); 8.38(d, 1H); 12.76(s, 1H)**** |
| 20. | 3,5-difluorophenyl | OH, H | $CH_3(CH_2)_2-$ (S) | $-COR_6$ | (3-methylpyridin-2-yl-S-phenyl) | $OCH_3$ | — | MH+ 613 |

-continued (I)

| N° | R₁ | R₂, R'₂ | R₃ | R₄ | R₅ | R₆ | R₇, R₈ |
|---|---|---|---|---|---|---|---|
| 21. | (CH₃)₃C— | OH, H(S) | CH₃(CH₂)₂— (S) | 2-benzylphenyl | —COR₆ | OCH₂CH₃ | — 552 |
| 22. | 3,5-difluorophenyl | H, H | CH₃(CH₂)₂— (S) | 2-benzylphenyl | —COR₆ | OCH₂CH₃ | — 592 |
| 23. | 3,5-difluorophenyl | H, H | CH₃(CH₂)₂— (S) | 2-methyl-4'-(trifluoromethyl)biphenyl | —COR₆ | OCH₂CH₃ | — 646 |
| 24. | (CH₃)₃C— | OH, H(S) | CH₃(CH₂)₂— (S) | 2-methyl-4'-(trifluoromethyl)biphenyl | —COR₆ | OCH₂CH₃ | — 606 |
| 25. | (CH₃)₃C— | OH, H(S) | CH₃(CH₂)₂— (S) | 3-methyl-2-(phenylthio)pyridinyl | —COR₆ | OCH₂CH₃ | — 571 |

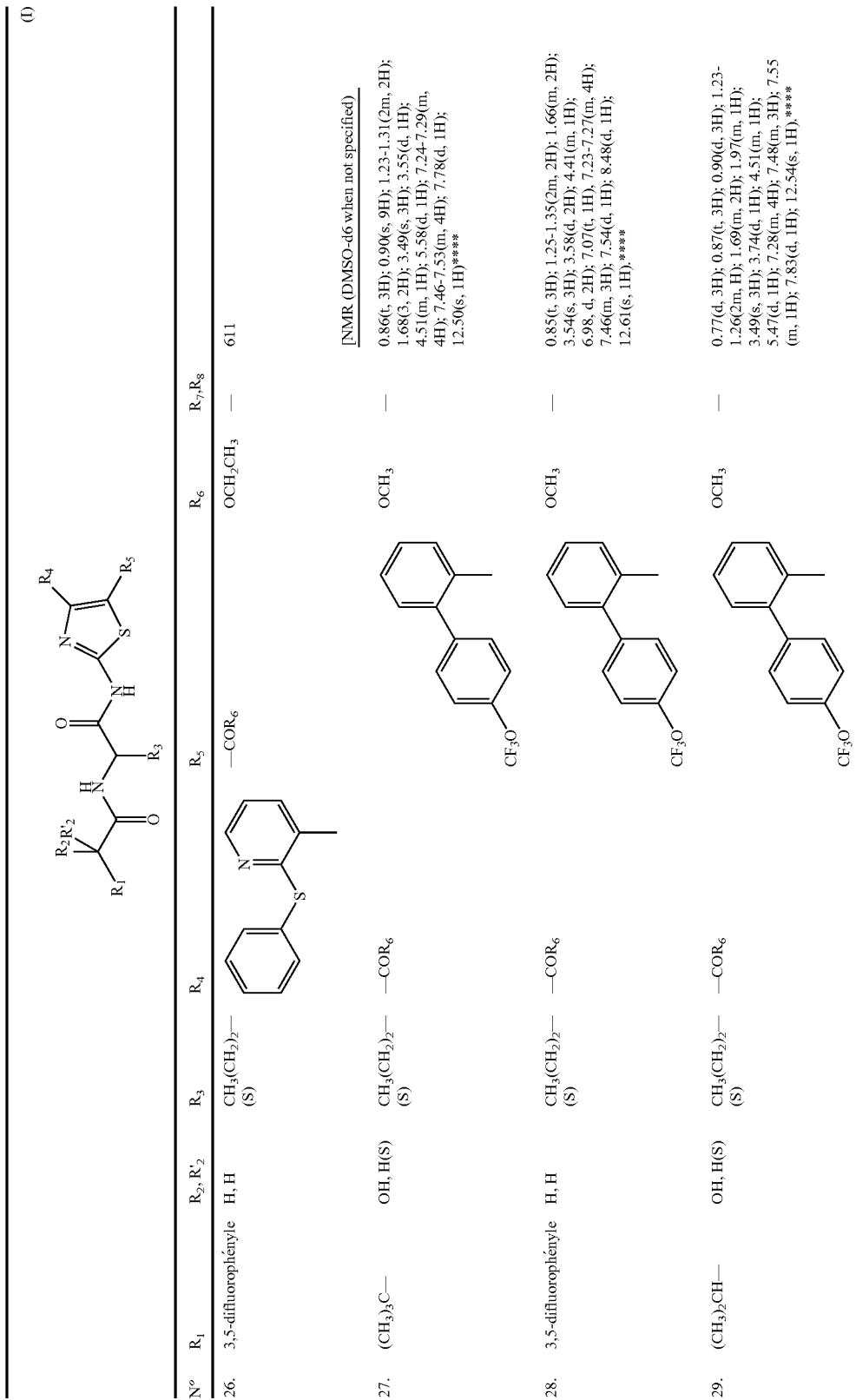

-continued (I)

| N° | R₁ | R₂,R'₂ | R₃ | R₄ | R₅ | R₆ | R₇,R₈ |
|---|---|---|---|---|---|---|---|
| 30. | (CH₃)₃C— | OH, H(S) | CH₃(CH₂)₂— (S) | —COR₆ | [2-methyl-4-(4-trifluoromethoxyphenoxy)phenyl] | OCH₃ | — 0.79(t, 3H); 0.82(s, 9H); 1.17-1.25(m, 2H); 1.63(m, 2H); 3.48(d, 1H); 3.58(s, 3H); 4.46(d broad, 1H); 5.52(d, H); 6.89(d, 2H); 7.01(t, 1H); 7.24(m, 3H); 7.44(m, 2H); 7.76(d, 1H); 12.55(s broad, 1H).*** |
| 31. | (CH₃)₂CH— | OH, H(S) | CH₃(CH₂)₂— (S) | —COR₆ | [2-methyl-4-(4-trifluoromethoxyphenoxy)phenyl] | OCH₃ | — 0.79(d, 3H); 0.90(d, 3H); 0.93(d, 3H); 1.30-1.40(m, 2H); 1.77(m, 2H); 2.05(m, H); 3.70(s, 3H); 3.80(d, 1H); 4.58(d, 1H); 5.58 (d, 1H); 7.02 d, 2H); 7.12(d, 1H); 7.35 (m, 3H); 7.55 m, 2H); 7.92(d, 1H); 12.70 (s, H).*** |

*means 300 MHz - means 360 MHz - *means 500 MHz - ****means 600 MHz

In the table:
- (S) or (R) in the columns "$R_3{}^1$" and "$R_2, R'_2$" indicate the stereochemistry of the asymmetric carbon, bearing $R_3$ or $R_2$, in formula (I). For the carbon bearing $R_2$, the indication (S) or (R) does not concern the case in which $R_2$ and $R'_2$ together form an oxo group;
- $MH^+$ is the value of the mass of the compound protonated with a hydrogen atom (mass of the compound+1), determined by LC-MS.

The compounds of the invention underwent pharmacological tests which showed their value as therapeutically active substances.

They were in particular tested as regards their effects of inhibiting the production of the β-amyloid (β-A4) peptide.

The β-amyloid (β-A4) peptide is a fragment of a larger precursor protein known as APP (Amyloid Precursor Protein). This protein is produced and present in various cells of animal or human tissue. However, its cleavage, in cerebral tissue, by enzymes of protease type leads to formation of the β-A4 peptide which accumulates in the form of amyloid plaque. The two proteases responsible for the production of the amyloid peptide are known as beta and gamma-secretases (Wolfe M S, Secretase targets for Alzheimer's disease: identification and therapeutic potential, J. Med. Chem., 2001, 44(13): 2039-60).

Now, it has been demonstrated that this gradual deposition of the β-A4 peptide is neurotoxic and might play an important role in Alzheimer's disease.

Thus, the compounds of the present invention, as inhibitors of the production of the β-amyloid (β-A4) peptide by inhibition of gamma-secretase, may be used in the treatment of pathologies such as senile dementia, Alzheimer's disease, Down's syndrome, Parkinson's disease, amyloid angiopathy and/or cerebrovascular disorders, frontotemporal dementia and Pick's disease, post-traumatic dementia, pathologies associated with neuroinflammatory processes, Huntington's disease and Korsakov's syndrome.

The tests were performed according to the protocol described below.

For the β-amyloid cellular test, the line CHO-K1 co-expressing the CT100 of APP and PS1 M146L clone 30-12 is used. The line targets the inhibition of gamma-secretase. Presenilin is associated with gamma-secretase activity (Wolfe M S, Haass C., The Role of presenilins in gamma-secretase activity, (J. Biol. Chem. 2001, 276(8): 5413-6) and its co-expression with the amyloid protein and its N-terminal fragment results in an increase in secretion of the A1-42 (β-A4) peptide, thus generating a pharmacological tool for evaluating the inhibition, by the compounds of formula (I), of the production of the β-A4 peptide. The inoculation of 96-well culture plates is performed at a rate of $1\times10^5$ cells per well in 150 µl of incubation medium. The presence of a minimum percentage (1.3% final) of serum allows cellular adhesion to the plastic after 2-3 hours of incubation at 37° C., in the presence of 5% $CO_2$. The products (15 µl) are tested at a final concentration of 10 µM 1% DMSO and are incubated for 24-25 hours at 37° C. in the presence of 5% $CO_2$ and 100% humidity. After this incubation of 24-25 hours, the cell supernatants (100 µl) are transferred into ELISA plates, treated with the uptake antibody 6E10 (6E10, epitope: aa1-17, INTERCHIM/SENETEK 320-10) to determine the level of amyloid peptides secreted by the cells in the presence of compounds according to the invention. A range of control peptide, "peptide 1-40", synthetic at 5 and 10 ng/ml is treated in parallel. The ELISA plates are incubated overnight at 4° C.

The amount of bound peptide is detected indirectly in the presence of a competitor corresponding to the truncated peptide, the biotin-coupled peptide 1-28, which is then detected with alkaline phosphatase-coupled streptavidin. The substrate, p-nitrophenyl phosphate (pNPP FAST p-Nitrophenyl Phosphate, Sigma N2770) gives a yellow soluble reaction product that can be read at 405 nm. The reaction is quenched with 0.1M EDTA solution. To do this, after binding the amyloid peptide on the ELISA plate, 50 µl of biotinylated peptide 1-28 are added to 100 µl of cell supernatant and incubated for 30 minutes at room temperature. The ELISA plates are then washed 3 times. After drying by inverting over absorbent paper, 100 µl of streptavidin-alkaline phosphatase (Interchim/Jackson ImmunoResearch Laboratories 016-050-084) are added per well and incubated for 1 hour at room temperature. The plates are washed again and the alkaline phosphatase substrate (pNPP 1 mg/ml) is added at a rate of 100 µl per well. After incubation for 30 minutes at room temperature, the reaction is quenched by adding 100 µl per well of 0.1M EDTA and the reading is taken at 405 nm.

The compounds of formula (I) according to the present invention that are the most active showed an $EC_{50}$ (50% effective concentration) of less than 500 nM and more particularly less than 100 nM. For example, compound 13 of the table showed an $EC_{50}$ of 6 nM.

The results of the biological tests show that the compounds are inhibitors of formation of the β-amyloid (β-A4) peptide.

Thus, these compounds may be used in the treatment of pathologies in which an inhibitor of formation of the β-amyloid (β-A4) peptide provides a therapeutic benefit. Such pathologies are especially senile dementia, Alzheimer's disease, Down's syndrome, Parkinson's disease, amyloid angiopathy, cerebrovascular disorders, frontotemporal dementia and Pick's disease, post-traumatic dementia, pathologies associated with neuro-inflammatory processes, Huntington's disease and Korsakov's syndrome.

The use of the compounds according to the invention for the preparation of a medicament for treating the pathologies mentioned above forms an integral part of the invention.

A subject of the invention is also medicaments comprising a compound of formula (I), or an addition salt thereof with a pharmaceutically acceptable acid, or alternatively a hydrate or a solvate of the compound of formula (I). These medicaments find their use in therapy, especially in the treatment of the pathologies mentioned above.

According to another of its aspects, the present invention relates to pharmaceutical compositions containing as active principle at least one compound according to the invention. These pharmaceutical compositions contain an effective dose of a compound according to the invention, or a pharmaceutically acceptable salt thereof, a hydrate or a solvate of the said compound, and optionally one or more pharmaceutically acceptable excipients.

The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the possible salt, solvate or hydrate thereof, may be administered in a unit form of administration, as a mixture with standard pharmaceutical excipients, to animals and humans for the prophylaxis or treatment of the above disorders or diseases.

The appropriate unit forms of administration include oral forms such as tablets, soft or hard gel capsules, powders, granules, chewing gums and oral solutions or suspensions, sublingual, buccal, intratracheal, intraocular or intranasal administration forms, forms for administration by inhalation, subcutaneous, intramuscular or intravenous administration forms and rectal or vaginal administration forms. For topical application, the compounds according to the invention may be used in creams, ointments or lotions.

By way of example, a unit form of administration of a compound according to the invention in the form of a tablet may comprise the following components:

| Compound according to the invention | 50.0 mg |
| --- | --- |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

In order to obtain the desired prophylactic or therapeutic effects, the dose of active principle may range between 0.1 mg and 200 mg per kg of body weight and per day. Although these dosages are examples of an average situation, there may be particular cases in which higher or lower dosages are appropriate, and such dosages are also included in the invention. According to the usual practice, the dosage that is appropriate to each patient is determined by the doctor according to the mode of administration and the weight and response of the said patient.

Each unit dose may contain from 0.1 to 1000 mg and preferably from 0.1 to 500 mg of active principle in combination with one or more pharmaceutical excipients. This unit dose may be administered 1 to 5 times a day so as to administer a daily dosage of from 0.5 to 5000 mg and preferably from 0.5 to 2500 mg.

According to another of its aspects, the present invention also relates to a method for treating the pathologies indicated above, which comprises the administration of a compound according to the invention, a pharmaceutically acceptable salt or a hydrate of the said compound.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound of the formula (I):

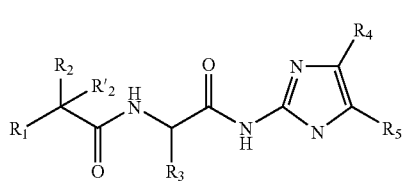

wherein $R_1$ represents:

either a $C_{1-6}$ alkyl optionally substituted with one to three substituents chosen from halogen, trifluoromethyl, hydroxyl, $C_{1-6}$ alkoxy, $C_{1-6}$ thioalkyl, thiophene or a phenyl;

or $C_{3-7}$ cycloalkyl, thiophene, benzothiophene, pyridyl, furyl or phenyl; said phenyl being optionally substituted with one to three substituents chosen from halogen atom, $C_{1-6}$ alkyl, $C_{1-6}$ alkoxy, hydroxyl, methylenedioxy, phenoxy, benzyloxy or trifluoromethyl;

$R_2$ and $R'_2$ represent, independently of each other, hydrogen, halogen, hydroxyl, $C_{1-3}$ alkoxy, $C_{1-3}$ alkyl, $C_{3-7}$ cycloalkyl, O—C(O)—$C_{1-6}$ alkyl;

or $R_2$ and $R'_2$ together form an oxo group;

$R_3$ represents hydrogen, $C_{1-6}$ alkyl optionally substituted with hydroxyl, $C_{1-6}$ cycloalkyl or $C_{1-3}$ alkoxy;

one or other of $R_4$ and $R_5$ represents a group Z:

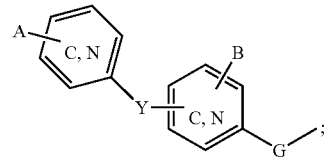

and one or other of $R_4$ and $R_5$ represents a group —C(X)$R_6$;

wherein

G represents a single bond or —$CH_2$—;

Y represents a single bond, oxygen or sulfur, $C_{1-4}$ alkylene or —N(W)—; said —$C_{1-4}$ alkylene-group being optionally substituted with hydroxyl or $C_{1-3}$ alkoxy; and wherein W represents hydrogen, $C_{1-3}$ alkyl optionally substituted with phenyl, or phenyl;

A and B represent, independently of each other, hydrogen or halogen, hydroxyl, $C_{1-3}$ alkyl, $C_{1-3}$ alkoxy, trifluoromethyl, trifluoromethoxy or —O—$CHF_2$;

X represents oxygen or sulfur;

$R_6$ represents $C_{1-6}$ alkoxy, hydroxyl or —$NR_7R_8$; said $C_{1-6}$ alkoxy group is optionally substituted with phenyl; and $R_7$ and $R_8$ represent, independently of each other, hydrogen; $C_{1-6}$ alkyl optionally substituted with $C_{3-7}$ cycloalkyl, $C_{3-7}$ cycloalkenyl, $C_{1-3}$ alkoxy, phenyl, morpholinyl or pyridyl; or $C_{3-7}$ cycloalkyl, $C_{1-6}$ alkoxy or phenyl; said $C_{3-7}$ cycloalkyl and phenyl are optionally substituted with one or two substituents chosen from halogen, hydroxyl, $C_{1-3}$ alkyl and $C_{1-3}$ alkoxy; or $R_7$ and $R_8$, with the nitrogen atom that bears them, form an aziridine, azetidine, pyrrolidine, piperidine, morpholine or benzopiperidine ring; or said compound in the form of a salt, hydrate or a solvate; and with the proviso that when Y is a single bond or oxygen and Z is

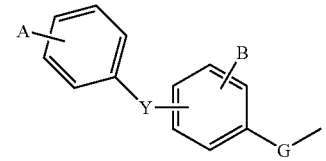

then A is other than hydrogen.

2. The compound according to claim 1, wherein $R_1$ represents $C_{1-6}$ alkyl or phenyl optionally substituted with one to three halogens; or a salt, hydrate or solvate thereof.

3. The compound of formula (I) according to claim 1, wherein $R_2$ and $R'_2$ represent, independently of each other, hydrogen or hydroxyl, or $R_2$ and $R'_2$ together form an oxo group; or a salt, hydrate or solvate thereof.

4. The compound of formula (I) according to claim 1, wherein $R_3$ represents $C_{1-6}$ alkyl; or a salt, hydrate or solvate thereof.

5. The compound of formula (I) according to claim 1, wherein:
$R_1$ represents $C_{1-6}$ alkyl or phenyl optionally substituted with one to three halogens;
$R_2$ and $R'_2$ represent, independently of each other, hydrogen or hydroxyl;
or $R_2$ and $R'_2$ together form an oxo group; and
$R_3$ represents $C_{1-6}$ alkyl;
or a salt, hydrate or solvate thereof.

6. The compound of formula (I) according to claim 1, wherein:
one or other of $R_4$ and $R_5$ represents a group Z

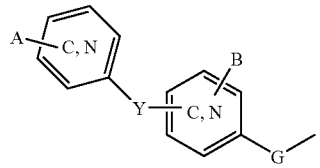
(Z)

and one or other of $R_4$ and $R_5$ represents a group —C(X)$R_6$;
G represents a single bond;
Y represents a single bond, oxygen or sulfur, or $C_{1-4}$ alkylene;
A and B represent, independently of each other, hydrogen, halogen, or trifluoromethyl or trifluoromethoxy;
X represents oxygen or sulfur; and
$R_6$ represents $C_{1-6}$ alkoxy; or
said compound in the form of a salt, hydrate or solvate; and with the proviso that when Y is a single bond or oxygen and Z is

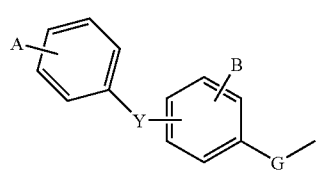
(Z)

then A is other than hydrogen.

7. The compound of formula (I) according to claim 1, wherein:
$R_1$ represents $C_{1-6}$ alkyl or phenyl optionally substituted with one to three halogens;
$R_2$ and $R'_2$ represent, independently of each other, hydrogen or hydroxyl;
or $R_2$ and $R'_2$ together form an oxo group; and
$R_3$ represents $C_{1-6}$ alkyl;
one or other of $R_4$ and $R_5$ represents a group Z

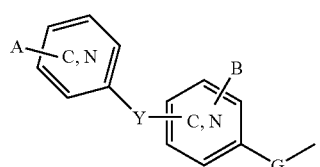
(Z)

and one or other of $R_4$ and $R_5$ represents a group —C(X)$R_6$;
G represents a single bond;
Y represents a single bond, oxygen or sulfur, or $C_{1-4}$ alkylene;
A and B represent, independently of each other, hydrogen, halogen, or trifluoromethyl or trifluoromethoxy;
X represents oxygen or sulfur; and
$R_6$ represents $C_{1-6}$ alkoxy; or
said compound in the form of a salt, hydrate or solvate; and with the proviso that when Y is a single bond or oxygen and Z is

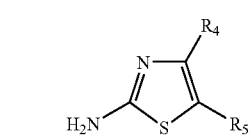
(Z)

then A is other than hydrogen.

8. A process for preparing a compound of formula (I) according to claim 1, comprising the step of:
forming a peptide coupling of 2-aminothiazole of formula (III)

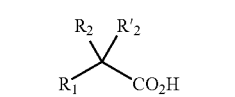
(III)

with an acylamino acid of formula (II)

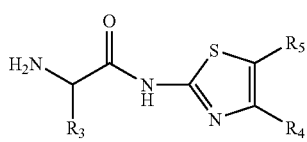
(II)

in which $R_1$, $R_2$, $R'_2$, $R_3$, $R_4$ and $R_5$ are as defined in formula (I) according to claim 1.

9. A process for preparing a compound of formula (I) according to claim 1, comprising the step of: performing a peptide coupling of a compound of formula (IV)

(IV)

with an amine of formula (VI)

(VI)

in which $R_1$, $R_2$, $R'_2$, $R_3$, $R_4$ and $R_5$ are as defined in formula (I) according to claim 1.

10. A pharmaceutical composition comprising at least one compound of formula (I) according to claim 1, or a pharmaceutically acceptable salt, hydrate or solvate thereof, in combination with one or more pharmaceutically acceptable excipients.

11. A pharmaceutical composition comprising at least one compound of formula (I) according to claim 5, or a pharmaceutically acceptable salt, hydrate or solvate thereof, in combination with one or more pharmaceutically acceptable excipients.

12. A pharmaceutical composition comprising at least one compound of formula (I) according to claim 6, or a pharmaceutically acceptable salt, hydrate or solvate thereof, in combination with one or more pharmaceutically acceptable excipients.

13. A pharmaceutical composition comprising at least one compound of formula (I) according to claim 7, or a pharmaceutically acceptable salt, hydrate or solvate thereof, in combination with one or more pharmaceutically acceptable excipients.

14. A method of treating a disease comprising administering to a patient in need of said treatment a therapeutically effective amount of a compound of formula (I) according to claim 1, or a pharmaceutically acceptable salt, hydrate or solvate thereof, wherein said disease is selected from the group consisting of senile dementia, Alzheimer's disease, Down's syndrome, Parkinson's disease, amyloid angiopathy, cerebrovascular disorder, frontotemporal dementia, Pick's disease, post-traumatic dementia, Huntington's disease and Korsakov's syndrome.

15. The method according to claim 14, wherein said disease is senile dementia.

16. The method according to claim 14, wherein said disease is Alzheimer's disease.

17. The method according to claim 14, wherein said disease is Down's syndrome.

18. The method according to claim 14, wherein said disease is Parkinson's disease.

19. The method according to claim 14, wherein said disease is amyloid angiopathy.

20. The method according to claim 14, wherein said disease is Pick's disease.

* * * * *

UNITED STATES PATENT AND TRADEMARK OFFICE
CERTIFICATE OF CORRECTION

PATENT NO. : 7,582,664 B2
APPLICATION NO. : 11/456123
DATED : September 1, 2009
INVENTOR(S) : Sylvie Baltzer et al.

Page 1 of 2

It is certified that error appears in the above-identified patent and that said Letters Patent is hereby corrected as shown below:

On the first page, in field (56), in column 2, under "Other Publications", line 1, delete "Encyclopaedic" and insert -- Encyclopedic --, therefor.

In column 4, line 27, delete "groups" and insert -- group --, therefor.

In column 6, line 25-26, in Structure (III), delete "  " and insert -- --, therefor.

In column 6, line 35-36, in Structure (VI), delete " 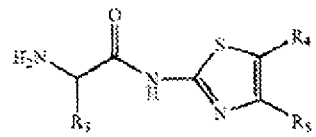 " and insert -- 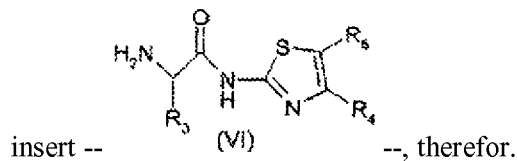 --, therefor.

Signed and Sealed this
Eighth Day of May, 2012

David J. Kappos
*Director of the United States Patent and Trademark Office*

CERTIFICATE OF CORRECTION (continued)
U.S. Pat. No. 7,582,664 B2

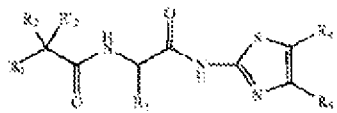

In column 6, line 45-46, in Structure (I), delete "  " and

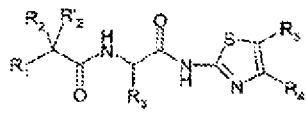

insert --  --, therefor.

In column 7, line 55-60, in Structure (XV), Scheme 4, delete " 2) $R_6COCH_2CO_2K, (XVIa)$," and insert -- 2) $R_6COCH_2CO_2K$ (XVIa), --, therefor.

In column 8, line 7, delete "Perkin 1," and insert -- Perkin I, --, therefor.

In column 10, line 30, delete "Compound" and insert -- compound --, therefor.

In column 13, line 52, delete "Compound" and insert -- compound --, therefor.

In column 14, line 24, delete "(d, 1H)" and insert -- (d, 1H). --, therefor.

In column 14, line 41, delete "phenyl-thio" and insert -- phenylthio --, therefor.

In column 16, line 18, delete "Compound" and insert -- compound --, therefor.

In column 33, line 2, delete "$R_3^1$" and insert -- $R_3$ --, therefor.

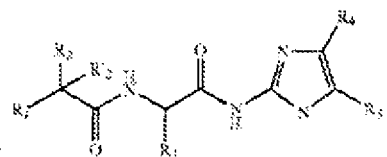

In column 35, line 52-54, in claim 1, delete "  " and insert -- 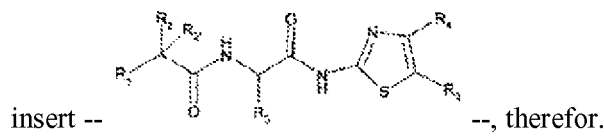 --, therefor.